(12) United States Patent
Walters et al.

(10) Patent No.: US 6,296,769 B1
(45) Date of Patent: Oct. 2, 2001

(54) MULTI-CHAMBERED SUPERCRITICAL FLUID EXTRACTION CARTRIDGE AND PROCESSES USING IT

(75) Inventors: Henry Walters; Dale Messer; Dale Clay; Robert W. Allington, all of Lincoln, NE (US)

(73) Assignee: Isco, Inc., Lincoln, NE (US)

( * ) Notice: Subject to any disclaimer, the term of this patent is extended or adjusted under 35 U.S.C. 154(b) by 0 days.

(21) Appl. No.: 09/366,128

(22) Filed: Aug. 2, 1999

Related U.S. Application Data

(60) Division of application No. 08/609,345, filed on Mar. 1, 1996, now Pat. No. 5,932,095, which is a continuation-in-part of application No. 08/215,259, filed on Mar. 21, 1994, which is a division of application No. 07/966,083, filed on Oct. 23, 1992, now Pat. No. 5,250,195, which is a continuation-in-part of application No. 07/847,652, filed on Mar. 5, 1992, now Pat. No. 5,173,188, which is a continuation-in-part of application No. 07/795,987, filed on Nov. 22, 1991, now Pat. No. 5,160,624, which is a continuation-in-part of application No. 07/553,119, filed on Jul. 13, 1990, now Pat. No. 5,094,753.

(51) Int. Cl.[7] ............................. B01D 11/02; B01D 35/00
(52) U.S. Cl. ..................... 210/637; 210/634; 422/256; 220/200
(58) Field of Search ................................. 210/198.2, 137, 210/200, 206, 634, 637, 644, 656; 422/256; 220/200

(56) References Cited

U.S. PATENT DOCUMENTS

| | | |
|---|---|---|
| 524,702 | 8/1894 | Browning . |
| 2,507,851 | 5/1950 | Bryant et al. . |
| 3,198,948 | 8/1965 | Olson . |
| 3,257,561 | 6/1966 | Packard et al. . |
| 3,872,723 | 3/1975 | Busch . |
| 4,032,445 | 6/1977 | Munk . |
| 4,064,908 | 12/1977 | Loe . |
| 4,217,931 | 8/1980 | Jaekel . |
| 4,225,290 | 9/1980 | Allington et al. . |
| 4,265,860 | 5/1981 | Jennings et al. . |

(List continued on next page.)

FOREIGN PATENT DOCUMENTS

| | | |
|---|---|---|
| 1357078 | 6/1974 | (CA) . |
| 124686 | 10/1967 | (CS) . |
| 40 02 161 A1 | 8/1991 | (DE) . |
| 0 212 999 A1 | 3/1987 | (EP) . |
| 0 236 982 A2 | 9/1987 | (EP) . |

(List continued on next page.)

OTHER PUBLICATIONS

Wright, B.W., et al., 1987, "Analytical Supercritical Fluid Extraction of Adsorbent Materials", Anal. Chem., 59:38–44.
Sugiyama, K., et al., 1985, "New Double–Stage Separation Analysis Method: Directly Coupled Laboratory–Scale Supercritical Fluid Extraction—Supercritical Chromatography, Monitored With A Multiwavelength Ultraviolet Detector", J. Chromatog., 332:107–116.

(List continued on next page.)

Primary Examiner—David A. Reifsnyder
(74) Attorney, Agent, or Firm—Vincent L. Carney

(57) ABSTRACT

A multiple chamber sample holding cartridge is used with a supercritical fluid extractor that causes membranes dividing the cartridge into chambers to rupture upon the pressurization of the sample cartridge, thereby allowing the intermixing of materials contained in the chambers. The neutral oil and loss determination of soybean and other oilseed oils by supercritical fluid extraction is efficient with this two-chambered sample cartridge.

12 Claims, 4 Drawing Sheets

U.S. PATENT DOCUMENTS

| | | |
|---|---|---|
| 4,375,163 | 3/1983 | Yang . |
| 4,476,732 | 10/1984 | Yang . |
| 4,477,266 | 10/1984 | Yang . |
| 4,483,773 | 11/1984 | Yang . |
| 4,564,145 | 1/1986 | Takada et al. . |
| 4,597,943 | 7/1986 | Sugiyama et al. . |
| 4,600,365 | 7/1986 | Riggenmann . |
| 4,676,897 | 6/1987 | Kuze et al. . |
| 4,705,459 | 11/1987 | Buisine et al. . |
| 4,711,764 | 12/1987 | Good . |
| 4,724,087 | 2/1988 | Perrut . |
| 4,770,780 | 9/1988 | Moses . |
| 4,790,236 | 12/1988 | Macdonald et al. . |
| 4,814,089 | 3/1989 | Kumar . |
| 4,820,129 | 4/1989 | Magnussen . |
| 4,851,683 | 7/1989 | Yang . |
| 4,871,453 | 10/1989 | Kumar . |
| 4,902,891 | 2/1990 | Vestal . |
| 4,913,624 | 4/1990 | Seki . |
| 4,915,591 | 4/1990 | Funke . |
| 4,984,602 | 1/1991 | Saito et al. . |
| 4,998,433 | 3/1991 | Stumpf et al. . |
| 5,013,443 | 5/1991 | Higashidate et al. . |
| 5,031,448 | 7/1991 | Saito . |
| 5,075,017 | 12/1991 | Hossain et al. . |
| 5,087,360 | 2/1992 | Wright et al. . |
| 5,094,741 | 3/1992 | Frank et al. . |
| 5,094,753 | 3/1992 | Allington et al. . |
| 5,116,508 | 5/1992 | Kumar et al. . |
| 5,133,859 | 7/1992 | Frank et al. . |
| 5,147,538 | 9/1992 | Wright et al. . |
| 5,151,178 | 9/1992 | Nickerson et al. . |
| 5,160,624 | 11/1992 | Clay et al. . |
| 5,164,693 | 11/1992 | Yokoyama et al. . |
| 5,173,188 | 12/1992 | Winter et al. . |
| 5,178,767 | 1/1993 | Nickerson et al. . |
| 5,180,487 | 1/1993 | Saito et al. . |
| 5,193,703 * | 3/1993 | Stats, III et al. .................... 210/656 |
| 5,193,991 | 3/1993 | Koebler et al. . |
| 5,198,197 | 3/1993 | Clay et al. . |
| 5,205,987 | 4/1993 | Ashraf-Khorassani et al. . |
| 5,240,603 | 8/1993 | Frank et al. . |
| 5,241,998 | 9/1993 | Ashraf-Khorassani . |
| 5,253,981 | 10/1993 | Yang . |
| 5,268,103 | 12/1993 | Jameson et al. . |
| 5,271,903 | 12/1993 | Durst et al. . |
| 5,316,262 | 5/1994 | Koebler . |
| 5,322,626 | 6/1994 | Frank et al. . |
| 5,363,886 | 11/1994 | Ashraf-Khorassani . |
| 5,372,716 | 12/1994 | Levy et al. . |
| 5,379,790 | 1/1995 | Bruce et al. . |
| 5,453,198 | 9/1995 | Ashruf-Khorassani et al. . |
| 5,458,783 | 10/1995 | Levy et al. . |

FOREIGN PATENT DOCUMENTS

| | | |
|---|---|---|
| 438 184 A1 | 1/1988 | (EP) . |
| 275933A2 | 7/1988 | (EP) . |
| 416326A2 | 3/1991 | (EP) . |
| 416326A3 | 3/1991 | (EP) . |
| 450182A2 | 10/1991 | (EP) . |
| 450182A3 | 10/1991 | (EP) . |
| 458125A2 | 11/1991 | (EP) . |
| 466 291 A3 | 1/1992 | (EP) . |
| 0 561 114 A1 | 9/1993 | (EP) . |
| 558172A2 | 9/1993 | (EP) . |
| 595 443 A1 | 5/1994 | (EP) . |
| 0 672 831 A2 | 9/1995 | (EP) . |
| 1552201 | 9/1979 | (GB) . |
| 2 254 383 | 10/1992 | (GB) . |
| 41424 | 3/1908 | (HU) . |
| 58-9317 | 2/1983 | (JP) . |
| 58-38115 | 3/1983 | (JP) . |
| 63-56425 | 3/1988 | (JP) . |
| 64-44847 | 2/1989 | (JP) . |
| 2-8039 | 1/1990 | (JP) . |
| 3-26531 | 2/1991 | (JP) . |
| 3-251435 | 11/1991 | (JP) . |
| 2 348 572 | 9/1973 | (NL) . |
| 463644 | 3/1975 | (SU) . |
| WO82/01578 | 5/1982 | (WO) . |
| WO 85/04816 | 11/1985 | (WO) . |
| WO 92/05851 | 4/1992 | (WO) . |
| WO92/06058 | 4/1992 | (WO) . |
| WO 94 08683 A1 | 4/1994 | (WO) . |
| WO 94/20190 | 9/1994 | (WO) . |
| WO 95/03106 | 2/1995 | (WO) . |

OTHER PUBLICATIONS

Hawthorne, S.B., et al., 1986, "Extraction and Recovery of Organic Pollutants from Environmental Solids and Tenax–GC Using Supercritical $CO_2$", J. Chromatog. Science, 24:258–264.

Hawthorne, S.B., et al., 1987, "Extraction and Recovery Polycyclic Aromatic Hydrocarbons from Environmental Solids Using Supercritical Fluids", Anal. Chem., 59:1705–1708.

Schantz, M.M. et al., "Supercritical Fluid Extraction Procedure for the Removal of Trace Organic Species from Solid Samples", J. Chromatogr., 363:397–401.

Wright, B.W., et al., 1989, "Supercritical Fluid Extraction of Coal Tar Contaminated Soil Samples", Energy & Fuels, 3:474–480.

Lee, M.L., et al., 1979, "Retention Indices for Programmed–Temperature Capillary–Column Gas Chromatography of Polycyclic Aromatic Hydrocarbons", Anal. Chem., 51(6):768–774.

Vassilaros, D.L., et al., 1982, "Linear Retention Index System For Polycyclic Aromatic Compounds", J. Chromatogr., 252:1–20.

Czubryt, J.J., et al., 1970, "Solubility Phenomna in Dense Carbon Dioxide Gas in the Range 270–1900 Atmospheres", J. Phys. Chem., 74(24):4260–4266.

Wise, S.A., et al., 1988, "Determination of Polycyclic Aromatic Hydrocarbons in a Coal Tar Standard Reference Material", Anal. Chem., 60:887–894.

Villaume, J.F., 1984, "Coal Tar Wastes: Their Environmental Fate and Effects", *Hazardous and Toxic Wastes: Technology, Management, and Health Effects,* Chapter 25, S.K. Majumdar and E.W. Miller, Eds., pp. 362–375.

Maxwell, R.J., et al., 1992, "Improved SFE Recovery of Trace Analytes from Liver Using an Intergral Micrometering Valve—SPE Column Holder Assembly", J. High Resolution Chromatogr., 15:807–811.

Levy, J.M., et al., 1990, "Qualitative Supercritical Fluid Extraction Coupled to Capillary Gas Chromatography", J. High Resolution Chromatogr., 13:418–421.

Levy, J.M., et al., 1991, "The Use of Alternative Fluids in On–Line Supercritical Fluid Extraction—Capillary Gas Chromatography", J. High Resolution Chromatog., 14:661–668.

Wright, B.W., et al., 1992, "Evaluation of a Field–Portable Supercritical Fluid Extraction Apparatus for Rapid Characterization of Contaminated Soils", *Waste Testing and Quality Assurance: Third Volume,* D. Friedman, Eds., pp. 3–14.

Richter, B.E., 1985, "Modified Flame Ionization Detector for the Analysis of Large Molecular Weight Polar Compounds by Capillary Supercritical Fluid Chromatography", J. High Resolution Chromatogr. & Chromatogr. Communications, 8:297–300.

Daimon, H., et al., 1991, "Directly Coupled Supercritical–Fluid Extraction/Capillary Supercritical–Fluid Chromatography of Polymer Additives", Chromatographia, 32:549–554.

Levy, J.M. et al., 1989, "Quantitative Supercritical Fluid Extraction Coupled to Capillary Gas Chromatography", Chromatographia, 28:613–616.

Nielen, M.W.F., et al., 1989, "On–line System for Supercritical Fluid Extraction and Capillary Gas Chromatography with Electron–Capture Detection", J. Chromatog., 474:388–395.

Raynor, M. W., et al., 1988, "Supercritical Fluid Extraction/Capillary Supercritical Fluid Chromatography/Fourier Transform Infrared Microspectrometry of Polycyclic Aromatic Compounds in a Coal Tar Pitch", J. High Resolution Chromatog. & Chromatog. Communications, 11:766–775.

Hawthorne, S.B., et al., 1989, "Coupled SFE–GC: A Rapid and Simple Technique for Extracting, Identifying, and Quantitative Organic Analytes from Solids and Sorbent Resins", J. Chromatog. Science, 27:347–354.

Berger, T.A., et al ., 1989, "Linear Velocity Control in Capillary Supercritical Fluid Chromatography by Restrictor Temperature Programming", J. Chromatog., 465:157–167.

Lipsky, S.R., et al., 1986, "High Temperature Gas Chromatography: The Development of New Aluminum Clad Flexible Fused Silica Glass Capillary Columns Coated with Thermostable Nonpolar Phases: Part 1", J. High Resolution Chromatog. & Chromatog. Communications, 9:376–382.

Green, S., et al., 1988, "Simple Restrictors for Capillary Column Supercritical Fluid Chromatography", J. High Resolution Chromatog. & Chromatog. Communications, 11:414–415.

Raynor, M.W., et al., 1988, "Preparation of Robust Tapered Restrictors for Capillary Supercritical Fluid Chromatography", J. High Resolution Chromatog. & Chromatog. Communications, 11:289–291.

Jinno, K., et al., 1991, "Coupling of Supercritical Fluid Extraction with Chromatography", Anal. Sci., 7:361–369.

Jentoft, R.E., et al., 1972, "Apparatus for Supercritical Fluid Chromatography with Carbon Dioxide as the Mobile Phase", Anal. Chem., 44:681–686.

Campbell, R.M., et al., 1986, "Supercritical Fluid Fractionation of Petroleum–and Coal–Derived Mixtures", Anal. Chem., 58:2247–2251.

Nam, K.S., et al., 1990, "Supercritical Fluid Extraction and Cleanup Procedures for Determination of Xenobiotics in Biological Samples", Chemosphere, 20:873–880.

Campbell, R.M., et al., "Supercritical Fluid Extraction of Chlorpyrifos Methyl from Wheat as Part per Billion Levels", J. Microcolumn Separations, 1:302–308.

Onuska, F.I., et al., 1989, "Supercritical Fluid Extraction of 2,3,7,8–Tetrachlorodibenzo–p–dioxin from Sediment Samples", J. High Resolution Chromatogr., 12:357–361.

Aida, T., et a l., 1987, "Organic Chemisty in Supercritical Fluid Solvents: Photoisomerization of trans–Stilbene", ACS Symposium Series 329, *Supercritical Fluids: Chemical and Engineering Principles and Applications,* T.G. Squires and M.E. Paulaitis, Eds., American Chemical Society, Chapter 5, pp. 58–66.

Barber, T.A., et al., 1990, "Solubility of Solid $Ccl_4$ in Supercritical $CF_4$ Using Directly Coupled Supercritical Fluid Extraction—Mass Spectrometry", Separation Science and Technology, 25:2033–2043.

Bond, N.D., 1981, "H–Coal Pilot Plant High Pressure and Temperature Letdown Valve Experience", Proc.of the 1981 Symposium on Instrumentation and Control for Fossil Energy Processes, Argonne National Lab. Report ANL 81–62, Jun. 8–10, pp. 654–679.

Bowman, L.M., 1976, "Dense Gas–Chromatographic Studies", Dessertation, Chapter 3, pp. 35–42.

Driskell, L., 1976, "Coping with High–Pressure Letdown", Chemical Engineering, 83:113–118.

Gardner, J.F., 1980, "Critical Valve Specifications and METC Valve–Testing Projects", Proc. of the 2nd Symposium on Valves for Coal Conversion and Utilization, DOE/MC/14522–1, Sec. 19.

Giddings, J.C., et al., 1977, "Exclusion Chromatography in Dense Gases: An Approach to Viscosity Optimization", Anal. Chem., 49:243–249.

pg,10

Grancher, et al., 1973, "The SNPA–DEA Process for the Desulfurization of High Pressure Gases", Proc. of the International Conference on Control of Gaseous Sulphur Compound Emission, Apr. 10–12. Hartmann, W., et al., 1977, "Fluid Chromatography of Oligomers", Proc. of the 6th AIRAPT International High Pressure Conference, *High Pressure Science and Technology,* K.D. Timmerhaus and M.S. Barber, Eds., pp. 573–582.

Hawthorne, S.B., et al., 1990, "Quantitative Analysis Using Directly Coupled Supercritical Fluid Extraction—Capillary Gas Chromatography (SFE–GC) With a Conventional Split/Splitless Injection Port", J. Chromatogr. Science, 28:2–8.

Hawthorne, S.B., et al., 1987, "Directly Coupled Supercritical Fluid Extraction—Gas Chromatographic Analysis of Polycyclic Aromatic Hydrocarbons and Polychlorinated Biphenyls from Environmental Solids", J. Chromatogr., 403:63–76.

Hirata, Y., et al., 1989, "Supercritical Fluid Extraction Combined with Microcolumn Liquid Chromatography for the Analysis of Polymer Activities", J. Microcolumn Separations; vol. 1, No. 1, 1989, pp. 46–50.

Illing, H.H., 1982, "Design Principles of Low Impingement Type Slurry Letdown Valves", Proc. of the 1982 Symposium on Instrumentation and Control for Fossil Energy Processes, Argonne National Lab. Report ANL 82–62, pp. 461–468.

Klesper, E., 1978, "Chromatography with Supercritical Fluids", Angew. Chem. Int. Ed. Eng., 17:738–746.

Klesper, E., et al., 1978, "Apparatus and Separations in Supercritical Fluid Chromatography", European Polymer Journal, 5:77–88.

Lapple, C.E., 1943, "Isothermal and Adiabatic Flow of Compressible Fluids", Trans. American Institute of Chemical Engineers, 39:385–432.

Liepmann, H.W., et al., "Flow in Ducts and Wind Tunnels", *Elements of Gasdynamics,* Chapter 5, pp. 124–143.

I. Moradinia, et al., 1987, "Solubilities of Five–Solid n–Alkanes in Supercritical Ethane", ACS Symposium Series 329, *Supercritical Fluids,* T.G. Squires and M.E. Paulaitis, Eds., American Chemical Society, Chapter 11, pp. 130–137.

Nair, J.B., et al., "On–Line Supercritical Sample–Preparation Accessory for Chromatography", LC–GC, 6:1071–1073.

Nilsson, W.B., et al., 1989, "Supercritical Fluid Carbon Dioxide Extraction in the Synthesis of Trieicosapentaenoylglycerol from Fish Oil", ACS Symposium Series 406, *Supercritical Fluid Science and Technology*, K.P. Johnston and J.M.L.Penninger, Eds., Chapter 5, pp. 89–108.

Platt, R.J., 1981, "High–Pressure Slurry–Letdown Valve Designs for Exxon Coal–Liquefaction Pilot Plant", Proc. Of the 2nd Symposium on Valves for Coal Conversion and Utilization, DOE/MC/14522–1, Sec. 6.

Rizvi, et al., 1988, "Concentration of Omega–3 Fatty Acids from Fish Oil Using Supercritical Carbon Dioxide", ACS Symposium Series 366, *Supercritical Fluid Extraction and Chromatography*, B.A. Charpentier and M.R. Sevenants, Eds., Chapter 5, pp. 89–108.

Saito, M., et al., "Fractionation by Coupled MicroSupercritical Fluid Extraction and Supercritical Fluid Chromatography", (Royal Soc. Chem. Chromatography Monographs), *Supercritical Fluid Chromatography*, R.M. Smith, 1988, Chapter 8, pp. 203–230.

Saito, M., et al., 1989, "Enrichment of Tocopherols in Wheat Germ by Directly Coupled Supercritical Fluid Extraction with Semipreparative Supercritical Fluid Chromatography", J. Chromatogr. Sci., 27:79–85.

Smith, R.D., et al., 1986, "Performance of Capillary Restrictors in Supercritical Fluid Chromatography", Anal. Chem., 58:2057–2064.

Temelli, F., et al., 1988, "Supercritical Carbon Dioxide Extraction of Terpenes from Orange Essential Oil", ACS Symposium Series 366, *Supercritical Fluid Extraction and Chromatography*, B.A. Charpentier and M.R. Sevenants, Eds., Chapter 6, pp. 109–126.

Wright, B.W., et al., 1988, "Analytical Supercritical Fluid Extraction Methodologies", ACS Symposium Series 366, *Supercritical Fluid Extraction and Chromatography*, B.A. Charpentier and M.R. Sevenants, Eds., Chapter 3, pp. 44–62.

Conoflow Corp. Valve Catalog sheets for 1968 and 1969.

Greibrokk, T., et al., 1984, "New System for Delivery of the Mobile Phase in Supercritical Fluid Chromatography", *Anal. Chem.*, 56:2681–2684.

Wheeler, J.R., et al., "Is SFC Worth the Effort?", *Res. & Dev.*; Chromatography; Feb.:134–138.

Hirata, Y., et al., "Direct Sample Injection in Supercritical Fluid Chromatography with Packed Fused Silica Column", *Journal of High Resolution Chromatography & Chromatography Communications*, vol. 11, Jan. 1988; pp. 81–84.

Berger, T.A., et al., "A New Supercritical Fluid Chromatograph", Paper 255, HPLC–92, 16th International Symposium on Column Liquid Chromatography, Lafayette, IN.

Thiebaut, D., et al., "Supercritical–Fluid Extraction of Aqueous Samples and On–Line Coupling to Supercritical–Fluid Chromatography", *On–Line Coupling of SFE and SFC*, 1989 Elsevier Science Publishers B.V.; pp. 151–159.

Wheeler, J. R., et al., "Supercritical Fluid Extraction and Chromatography of Representative Agriculture Products with Capillary and Microbore Columns", *Journal of Chromatographic Science*, vol. 27, Sep. 1969; pp. 534–539.

Lopez–Avila, Viorica, et al., "SFE/IR Method for the Determination of Petroleum Hydrocarbons in Soils and Sediments", Environmental Monitoring Systems Laboratory, Contract No. 68–C1–0029, Section 4, p. 8.

Levy, Joseph M., et al., "Multidimensional Supercritial Fluid Chromatography and Supercritical Fluid Extraction", *Journal of Chromatographic Science*, vol. 27, Jul. 1989, pp. 341–346.

Schwartz, H.E., et al., "Gradient Elution Chromatography with Microbore Columns", *Analytical Chemistry*, vol. 55, No. 11, Sep., 1983, pp. 1752–1760.

Schwartz, H.E., et al., "Comparison of Dynamic and Static Mixing Devices for Gradient Micro–HPLC", *Journal of Chromatographic Science*, vol. 23, Sep., 1985, pp. 402–406.

SFE–Plus Supercritical Fluid Extraction System brochure, Micro–Tech Scientific.

Kalinoski, Henry T., et al., "Supercritical Fluid Extraction and Direct Fluid Injection Mass Spectrometry for the Determination of Trichothecene Mycotoxins in Wheat Samples", *Anal. Chem.* 1986, 58, 2421–2422.

Ramsey, Edward D., et al., "Analysis of Drug Residues in Tissue by Combined Supercritical–Fluid Extraction—Supercritical–Fluid Chromatography—Mass Spectrometry—Mass Spectrometry", *Journal of Chromatography*, 464 (1989) 353–357.

Sims, Marc, et al., "Design and Control of CO2 Extraction Plants", presented at 2nd International Symposium on Supercritical Fluids, May 20–22, 1991, Boston, MA; pp. 1–8.

Lack, E., et al., "Findings and Experience Acquired in Operating Industrial High Pressure Extraction Plants with Supercritical CO2", pp. 473–480.

Engineered Pressure Systems Inc. "Supercritical Fluid Extraction" brochure.

SITEC brochure on HP–Spray Drying/Micronisation/Supercritical Extraction and pilot plants.

Brochure from Extract Company GMBH on "Extraction with super–critical gases" production plants.

Brochure "Hochdruck–Extraktion—$CO_2$" UHDE.

Korner, J.P., "New Developments in the Design and Construction of Industrial–size SCGE Plants", Proceedings of the International Symposium on Supercritical Fluids, Tome 1, Nice France, Oct. 17, 18, 19, 1988; pp. 633–641.

"Instruments for Separation and Analysis" Product Guide 12, Isco, Inc., Brochure 9501, Jan. 1995.

Suprex Corporation brochure "MPS/225".

Specs for Chassis for Ultra Plus Extrapolator by Micro–Tech Scientific, by F. Yang, Sep. 1994.

Yang, F. J., et al., "Design Concepts for a New Generation Supercritical Fluid Extraction System" Micro–Tech Scientific.

McNally, Mary Ellen P., et al., "Supercritical Fluid Extraction Coupled with Supercritical Fluid Chromatography for the Separation of Sulfonylurea Herbicides and their Metabolites from Complex Matrices", *Journal of Chromatography*, 435 (1988) 63–66.

Hawthorne, Steven, et al., "Analysis of Flavor and Fragrance Compounds Using Supercritical Fluid Extraction Coupled with Gas Chromatography", Anal. Chem., 1988, 60, 472–473.

Marc Simms S–F–E brochure on "Dense Gas Management System for Supercritical Fluid Extraction and Processing".

Cassat, D., et al., "Extraction of PCB from Contaminated Soils by Supercritical $CO_2$", International Symposium on Super–critical Fluids, Tome 2, Nice France, Oct. 17, 18, 19, 1988, pp. 771–776.

De Ruiter, C., et al., "Design and Evaluation of a Sandwich Phase Separator for On–Line Liquid/Liquid Extraction", *Analytica Chimica Acta,* 192(1987) pp. 267–275.

Advertisement "SFE Analyser 3000", Fisons Instruments SpA; LPI Mar./Apr. 1993.

"RIA" Bulletin 7250, Beckman Instruments.

"Concept 4" brochure; Micromedic Systems.

"The HP 7680A Supercritical Fluid Extractor" brochure; Hewlett–Packard.

"Supercritical Fluid (Dense Gas) Chromatography/Extraction with Linear Density Programming" Lyle M. Bowman, Jr., Marcus N. Myers, and J. Calvin Giddings; *Separation Science and Technology,* 17(1) (1982) 271–287.

"Microscale Supercritical Fluid Extraction and Coupling of Microscale Supercritical Fluid Extraction with Supercritical Fluid Chromatography" Muneo Saito, Toshinobu Hondo, Masaaki Senda, *Progress in HPLC* vol. 4 (1989) Yoshioka, et al. (Eds) pp. 87–110.

"Fractionation of Anhydrous Milk Fat by Superficial Carbon Dioxide" by Joseph Arul, Armand Boudreau, Joseph Makhlouf, Rene Tardif, and Madhu R. Sahasrabudhe, *Journal of Food Science,* vol. 52, No. 5, 1987, pp. 1231–1236.

"Grobtechnische Anlagen zur Extraktion mit uberkritischen Gasen" by Von R. Eggers; Angew. Chem. 90, 1978, pp. 799–802.

"New Pressure Regulating System for Constant Mass Flow Supercritical–Fluid Chromatography and Physico–Chemical Analysis of Mass–Flow Reduction in Pressure Programming by Analogous Circuit Model" by M. Saito, et al.; *Chromatographia* vol. 25, No. 9, Sep. 1988, pp. 801–805.

"Extraction with supercritical fluids: Why, how, and so what" Gale G. Hoyer; Chemtech, Jul. 1985, pp. 440–448.

Suprex AutoPrep 44 brochure (The AutoPrep 44 was on sale on or around late 1992).

"Portable Thermal Pump for Supercritical Fluid Delivery" *Analytical Chemistry* 67 (1995) Jan. 1, No. 1, pp. 212–219.

Suprex PrepMaster manual, pp. 8–1 to 8–12, May 1995.

Suprex AutoPrep 44 brochure, p. 6.

\* cited by examiner

MULTI-CHAMBERED SUPERCRITICAL FLUID EXTRACTION CARTRIDGE AND PROCESSES USING IT

RELATED CASES

This application is a divisional of U.S. patent application Ser. No. 08/609,345 filed Mar. 1, 1996 now U.S. Pat. No. 5,932,095, which is a continuation-in-part of U.S. patent application Ser. No. 08/215,259, filed Mar. 21, 1994 still pending, which is a divisional application of U.S. patent application Ser. No. 07/966,083, filed Oct. 23, 1992 now U.S. Pat. No. 5,250,195, which is a continuation-in-part of U.S. patent application Ser. No. 07/847,652 filed Mar. 5, 1992, now U.S. Pat. No. 5,173,188, which is a continuation-in-part of U.S. patent application Ser. No. 07/795,987 filed Nov. 22, 1991, now U.S. Pat. No. 5,160,624, which is a continuation-in-part of U.S. patent application Ser. No. 07/553,119, filed Jul. 13, 1990, now U.S. Pat. No. 5,094,753 for APPARATUS AND METHOD FOR SUPERCRITICAL FLUID EXTRACTION.

BACKGROUND OF THE INVENTION

This invention relates to supercritical fluid extraction and to assays of natural fats and oils, such as for example, neutral oil and loss determination for soybean and other oilseeds oils.

In supercritical fluid extraction, an extraction vessel is held at a temperature above the critical point and is supplied with fluid at pressure above the critical pressure. Under these conditions, the fluid within the extraction vessel is a supercritical fluid. In one type of apparatus for supercritical extraction, there is a specially constructed extraction vessel within a source of heat.

A prior art apparatus for supercritical extraction of this type is described by B. W. Wright, et al., in *ANAL. CHEM.* 59 38–44 (January, 1987) using a glass-lined extraction chamber within a bolted stainless steel extraction vessel heated in an oven. This type of extraction apparatus has the disadvantages of: (1) requiring time consuming steps to open the pressurized extraction vessel to insert the sample before use and again to open it after use to remove the spent sample; and (2) under some circumstances requiring the handling of a hot extraction vessel.

It is known how to determine or assay ratios of the components of oilseed oil to characterize the oilseed product. One method of making such an assay or determination is "neutral oil and loss determination."

In the prior art, natural oil and loss determinations are done with non-supercritical fluid extractor methods, such as for example, liquid chromatography, to estimate the amount of refinable oil present in crude oilseed oils. A liquid chromatography method, designated method CA 9f 57, for neutral oil and loss is approved by the American Oil Chemists Society.

In the method approved by the American Oil Chemists Society: (1) the oil is solubilized in an organic solvents; (2) the solubilized oil is passed through a bed of activated alumina separating medium where the polar components of the oil are absorbed; (3) the remaining solution is collected; (4) the neutral oil and loss residue solvents are removed; and (5) the value is determined by mass difference. The apparatus employed in the american Oil Chemists Society method CA 9f 57 is constructed entirely of glass with a gravity-fed solvent.

This current prior art method has several disadvantages such as: (1) large amount of organic solvents are consumed; (2) the method is time consuming; and (3) the alumina bed is prone to plugging.

Accordingly, it is an object of the invention to provide a novel supercritical fluid extraction system and method.

It is a further object of the invention to provide a two or more chambered supercritical fluid extraction cartridge separated by one or more rupture membranes.

It is a further object of the invention to provide a novel cartridge for supercritical fluid extractors.

It is a still further object of the invention to provide a novel supercritical fluid extraction system in which a multiple chamber cartridge is pressurized equally in the inside and the outside of the cartridge during extraction.

It is a still further object of the invention to provide a novel sample cartridge that can be opened and closed easily without the use of tools.

It is a still further object of the invention to provide a multiple chamber sample cartridge in which the chambers are separated by a membrane that can be easily removed and replaced.

It is a still further object of the invention to provide a novel supercritical fluid cartridge that may be reused.

It is a still further object of the invention to provide a novel cartridge for use in supercritical fluid extraction having multiple chambers and one or more separating membranes all of similar chemical makeup so that the fluid is exposed to common materials to avoid the introduction of possible reactants.

It is a still further object of the invention to provide a multiple chamber cartridge for use in supercritical fluid extraction, in which the membrane separating the chambers may be easily cleaned before use and is disposable to avoid contamination if the cartridge is reused.

It is a still further object of the invention to provide a multiple chamber cartridge for use in supercritical fluid extraction, in which the chambers are sealed by a membrane to prevent the migration of oils across, around and through the membrane prior to the beginning of fluid flow.

It is a still further object of the invention to provide a supercritical fluid extraction system in which a plurality of samples, prepared before the beginning of an extraction run and placed in a corresponding plurality of multiple-chamber sample cartridges, are automatically sequenced through the supercritical fluid extraction system with the contents of the individual chambers of each sample cartridge being isolated until pressurization of the sample cartridge within the supercritical fluid extraction system.

It is a still further object ofthe invention to provide a novel method for measuring neutral oil and loss.

It is a still further object of the invention to provide a novel method for determining or assaying the ratio of the components of oilseed using supercritical fluid extraction.

It is a still further object of the invention to provide novel apparatus useful in determining the components of certain mixtures using supercritical fluid extraction.

It is a still further object of the invention to provide cartridges for use in supercritical fluid extraction system possessing a volume of between 0.2 and 2,000 cubic centimeters.

In accordance with the above and further objectives of the invention, a supercritical fluid extraction system includes a cartridge capable of holding the sample to be extracted and a pressure vessel into which the cartridge fits. The pressure vessel fits into a heater and the cartridge is removably mounted in the pressure vessel. The pressure vessel and cartridge are held sealed by a breach plug for the pressure vessel. The sample cartridge should possess a volume of between 0.2 and 2,000 cubic centimeters and include multiple chambers which may be separated by a fluid tight membranes. Either multiple separate inlets or separate outlets are provided to permit equalization of pressure on the inside and the outside of the cartridge. In the preferred embodiment, the multiple openings are outlets to avoid contamination of extract from impurities outside of the cartridge but inside the pressure vessel.

In extracting oilseeds, a mulitple chamber cartridge may be utilized to extract the components of the oilseed. To achieve consistent results in this process, the oil and alumina are located in separate chambers of the cartridge, separated by a membrane. The membrane has a strength selected such as to rupture only upon pressurization of the inside of the cartridge This provides consistent imitation of the extraction of the neutral oil and selective deposition of the polar components of the oil onto the alumina bed and thus more predictable results.

SUMMARY OF THE DRAWINGS

The above-noted and other features of the invention will be better understood from the following detailed description when considered in connection with the accompanying drawings in which.

DETAILED DESCRIPTION

Figure 1:
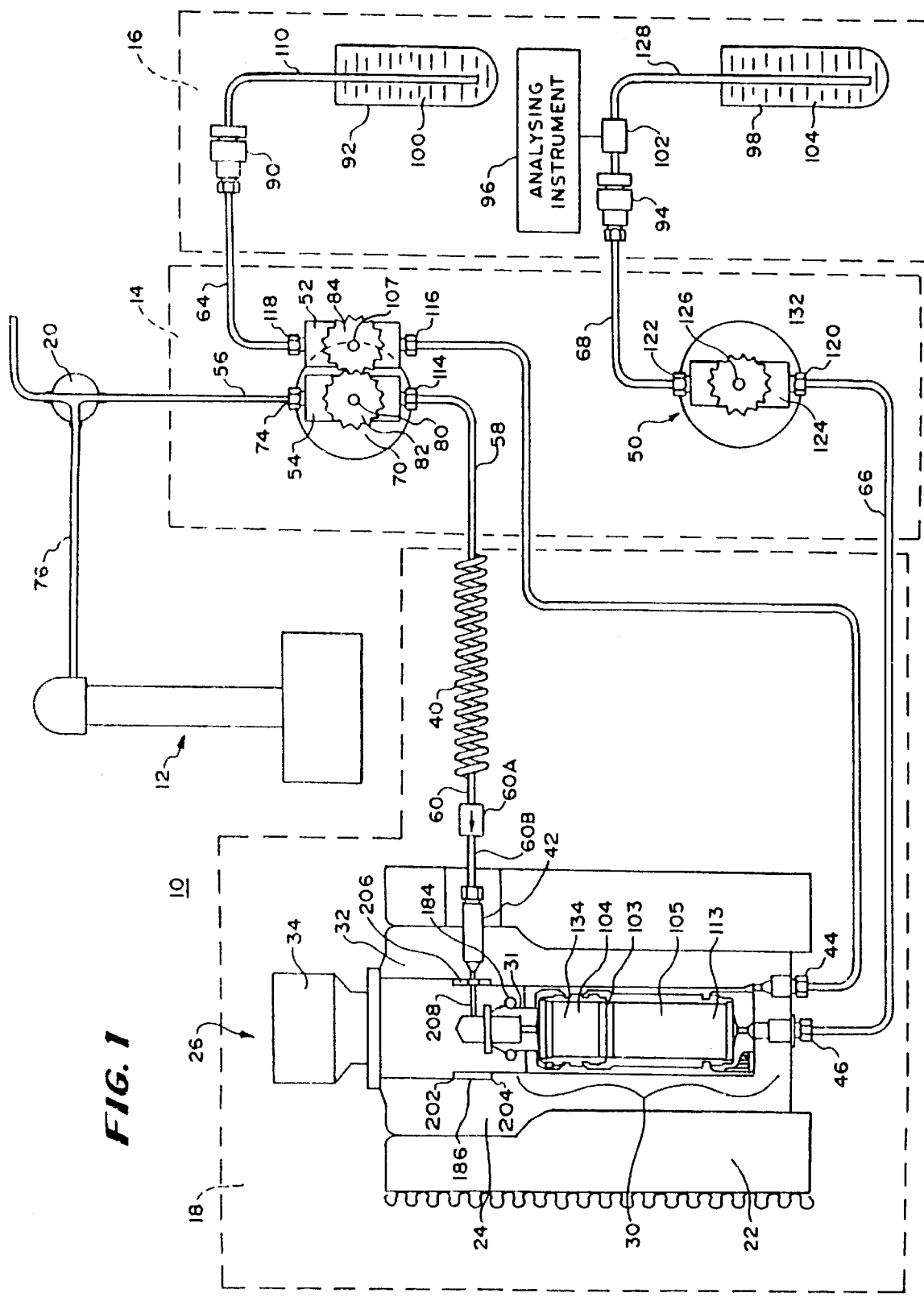
FIG. 1 is a schematic view of a supercritical fluid extraction system utilizing an embodiment of the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The pump system 12, the collector system 16, and the valve system 14 are not part of the invention except insofar as they cooperate with the pressure-vessel and fluid-extraction assembly 18. These components are disclosed in U.S. Pat. Nos. 5,094,753; 5,160,624; 5,173,188; 5,132,014; 5,250,195; 5,198,107; 5,296,145; 5,269,936; 5,268,102; 5,268,103; the disclosures of which are incorporated herein by reference.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12.

With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. This membrane separates the sampler 134 from additional modifiers, chemical or reactants 105 until the membrane is ruptured. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for efficient thermal transfer to the supercritical fluid and sample. With this arrangement, the heating block 22 maintains the fluids within the pressure-vessel and .pa fluid-extraction assembly 18 at supercritical fluid temperature and pressure for proper extraction.

In the preferred embodiment, the cartridge and plug assembly 26 includes a multichamber extraction cartridge assembly 30, a breech plug 32 and a knob 34 which are connected together so that: (1) the pressure vessel 24 is easily sealed with the breech plug 32; (2) the extraction cartridge assembly 30 snaps onto the opening 31 in the breech plug 32 where it is held by a garter spring 184 and the assembly may be carried by the knob 34 that threads into the pressure chamber; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge 30 and for the interior of the extraction cartridge 30 being provided through a groove circumscribing the assembly inside the pressure vessel 24.

An annular self-acting high pressure seal 202 cooperates with a sealing surface 186 to seal high pressure supercritical fluid from the atmosphere and an annular low pressure seal 204 spaced from the annular high pressure seal 202 prevents contaminated supercritical fluid in the space between the interior of the pressure vessel 24 and the exterior of the extraction cartridge assembly 30 from getting back to the supercritical fluid supply. These two annular seals 202 and 204 form between them a torroidal inlet chamber into which the outlet of the fluid inlet 42 extends to introduce fluid. Contamination may arise from fingerprints or other foreign material on the outside wall of extraction cartridge assembly 30 and the low pressure seal 204 protects against this contamination. Seals 202 and 204 are Bal-Seal type 504MB-118-GFP.

Supercritical fluid is supplied to fluid inlet 42 and circulates in the annular space between high pressure seal 202 and low pressure seal 204, and then follows two paths into the pressure vessel 24 and extraction cartridge 30; one path for purging and one path for extraction. An annular spacer 206 within the torroidal opening between seals 202 and 204 has an hour-glass shaped cross section with radial holes through it and distributes incoming supercritical fluid from the inlet of fitting 42 to the opposite side of the spacer 206 from which it flows to passageway 208 drilled in breech plug 32.

With this arrangement the multichamber extraction cartridge assembly 30 may be easily sealed in the pressure vessel 24 by threading the breech plug 32 into it and may be easily removed by unthreading the breech plug 32 and lifting the knob 34.

The extraction cartridge assembly 30 contains an inlet, an outlet, a plurality of chambers and at least one pressure sensitive seal between chambers. The chambers are formed in the hollow interior of the cartridge and each chamber is separated from another chamber between the inlet and the outlet by at least one pressure sensitive seal. The hollow interior is thus divided into at least two chambers separated by a pressure sensitive fluid seal such as a rupturable membrane with an inlet communicating with a chamber on one side of the membrane and an outlet communicating with a chamber on the other side of the membrane so that a sample to be extracted may be placed in the hollow interior and supercritical fluid passed through the inlet, the first chamber of the hollow interior, into the second chamber after pressure builds in the first chamber sufficient to break the membrane, and to the outlet to a collector.

The extraction cartridge assembly 30 serves as an extraction chamber or tube, the pressure vessel 24 serves as an extraction vessel and the heating block 22 serves as an oven as these terms are commonly used in the prior art. Multiple chambers and membranes may be located in series between the inlet and outlet to control the movement of supercritical fluid in stages depending on pressure build up and/or to separate liquid or solid ingredients, such as for example reactants and modifiers, until the membranes separating them are broken. The membranes may be of the same strength or may increase in strength according to their location so as to break sequentially as the pressure builds up. Thus the strength may weaken slightly from input to output to compensate for attenuation in solid separating material, or more commonly, increase to provide sequential breaking as the pressure builds between the inlet and the outlet.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although in the preferred embodiment the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section to effectively block any considerable amount of transfer of heat between the cartridge and the knob 34. It should have a heat conductivity no greater than 0.05 calories/cm. sec. degree C. at 30 degrees Centigrade.

The extraction cartridge assembly 30 has an opening that permits supercritical fluid to enter the pressure vessel 24 to follow and follow either of two paths. One path passes into the extraction cartridge or tube and out through an outlet of the extraction cartridge into a conduit leading to a collector. Other supercritical fluid follows the second path around the outside of the cartridge to remove contaminants from the pressure vessel 24, equalize pressure and flow through another outlet.

One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. In the preferred embodiment, the volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes along the narrow space outside the extraction cartridge assembly 30 past the garter spring 184 and sweeps the outside of the cartridge.

Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube. This feature allows for the membrane 103 to remain intact until flow through the extraction 30 begins. This flow is controlled by valve 50, and does not begin until valve 50 is opened.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings such as shown at 46. The inlet fittings such as shown at 42 and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 1) with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 56 carries pressurized fluid from the pumping system 12 to tee joint 20; (2) tube 76 is connected to one arm of tee joint 20 to carry pressurized fluid to another liquid extraction system unit not shown on FIG. 1; and (3) the remaining arm of the tee joint 20 is connected through the tube 56 to an inlet fitting 74 of extracting fluid valve 54. The valves 50, 52 and 54 are, in the preferred embodiment, SSI type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite .pa direction, the clockwise rotation of knob 70 opens purge fluid valve 52.

The relative locations of the two gears on the two shafts are such that, in the first (clockwise) position of the knob 70, the extracting fluid valve 54 is shut and the purge fluid valve 52 is open. Turning the control knob 70 counterclockwise 130 degrees from this first position opens extracting fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the conduit 66, the valve inlet fitting 120, the outlet fitting 122, through the tube 68 and into the collector system 16. The resulting pressure differential is the extraction cartridge assembly 30 causes the membrane 103 to rupture. In so doing, the sample is mixed with chemicals or reactants 105 at instance in time during the extraction.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through valve 50 flows through tube 68 to the extractant coupling 94 and from there to the capillary tube 128 and extractant fluid collector 98 which contains an appropriate solvent 104 in the preferred embodiment.

The analyzing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the extractant fluid collector 98 and information about its light absorbance. Other analytical instruments may also be used to identify or indicate other characteristics of the extractant.

Figure 2:
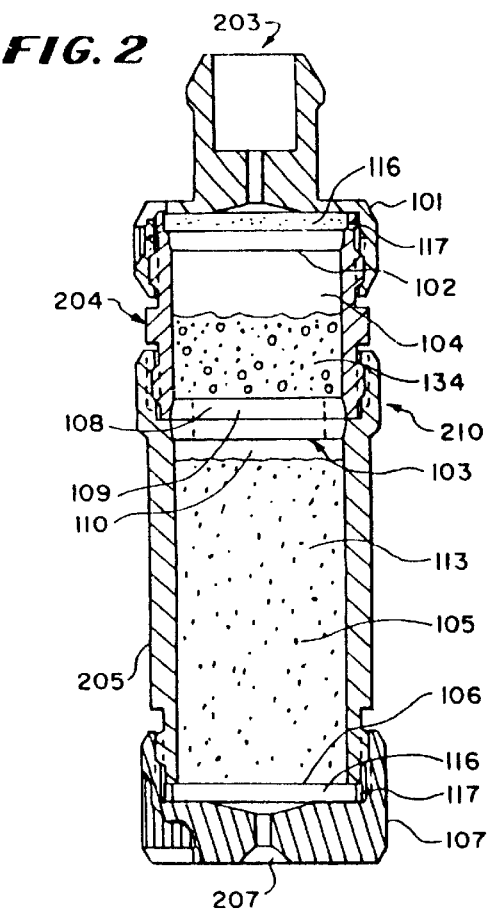
FIG. 2 is an elevational sectional view through the center of a cartridge utilized in the embodiment of FIG. 1.

FIG. 2 is a sectional elevational view of a sample cartridge 30 having two chambers 104 and 105. In the preferred embodiment, the cartridge includes cartridge caps, frits and sealing mechanisms as specified in U.S. Pat. Nos. 5,132,014; 5,173,188 and 5,296,145, the disclosures of which are incorporated herein by reference.

The first chamber 104 of the sample cartridge 30 is formed by a first cylindrical tubular body tube 204, a separating membrane assembly 109 and a frit 102 and the second chamber 105 is formed by a second tubular body 205, a frit 106 and the membrane assembly 109. The internal openings within the tubular chambers 104 and 105 are separated only by the membrane assembly so as to be bounded by connecting tubular wall portions 204 and 205 with the inlet of the cartridge 203 communicating through the frit 102 with the chamber 104 on a first side of the membrane assembly 103 and with the outlet 207 communicating with the second or lower chamber 105 to provide a fluid path when the membrane assembly 103 is ruptured by fluid flow from an inlet 203 to an outlet 207. The frit 102 is held in place by a top end cap 101 threaded on to the upper portion of the tube 204 and the lower frit 106 and is held in place by an end cap 107 threaded on to the tubular wall 105.

Figure 3:
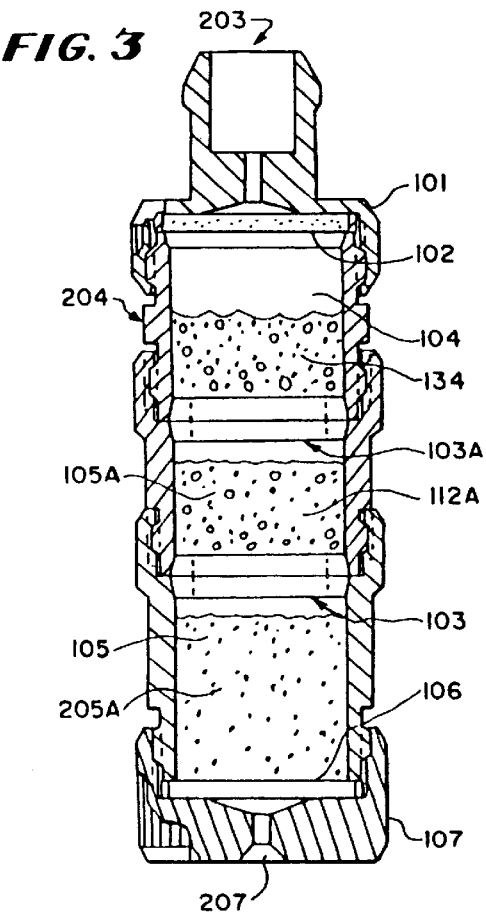
FIG. 3 is an elevational sectional view through the center of another cartridge used in another embodiment of the invention.

As shown in FIG. 3, the sample such as a liquid 134 is contained in the upper compartment 104 and another material such as a separating medium 113 is in the lower compartment. Tubes 204 and 205 thread or otherwise fasten together.

The upper chamber tube 204 has reduced diameter externally threaded top and bottom end portions and the lower chamber tube 205 has reduced diameter externally threaded bottom end portion and a shoulder to accommodate internally threaded top portion. The membrane assembly 103 and the inner wall of the cartridge where the tubes 204 and 205 are connected, are complementarilly formed to fit into each other and provide a seal. In the preferred embodiment, the matching interfitting parts of the sample cartridge and liquid tight rupture seal 103 have a 10 degree beveled angle. The liquid tight rupture seal 103, made up collectively of an upper holding ring 108, a membrane 109 and a lower holding ring 110 serves as a lower containment means. The separating medium 113 is contained in tube 105 by the rupture seal serving as the upper containment means and is contained at the bottom by means of a porus filter or frit 106 and bottom end cap 107.

In the preferred embodiment, the assembly consisting of the cartridge frame with end pieces 101 and 107, and compartment tubularwalls 204 and 205 is constructed from aluminum, stainless steel or a suitable polymer material. A liquid tight rupture seal 103 separates the upper and lower chambers. Internal frits or filters 102,106 are composed of an internal frit 116 and a sealing ring 117. Each internal frit has approximately the same diameter and is arranged to be in alignment with respect to its corresponding tube 204 or 205. Each frit ring 115 snugly fits its corresponding frit and has an external diameter that is slightly less than the internal diameter of the corresponding cartridge end caps 101 and 107. Cartridge end caps 101 and 107 are internally threaded or fastened in a manner to press the sealing ring between the cartridge face and the end caps.

In FIG. 3, there is shown a longitudinal sectional view of another embodiment, 30A of extraction cartridge. This embodiment has many parts the same as other embodiments but instead of having two chambers and one membrane, it has three chambers and two membranes. The first chamber 104 includes sample and is closest to the inlet 203 to be the first to receive supercritical fluid as it is pumped by the pumping system. The second compartment 105A includes a reactant or modifier and the third compartment 105 is similar to 105 in FIG. 2 and may include a granular separating material. The first and second compartments 104 and 105A are connected in series in that order and the second compartment 105A is sealed from the first compartment by a membrane assembly 103A. The lower compartment 105 is separated from the second compartment 105A by another membrane assembly 103.

With this arrangement, supercritical fluid is pumped into the inlet 203 until pressure builds up and ruptures the membrane within the first membrane assembly 103A, after which, pressure builds up in the second of the series of compartments 105A. When this pressure builds above the design strength of the membrane 103, the membrane 103 ruptures and the supercritical fluid flows through the last compartment and out of the outlet 207. The membranes may have the same design strength, or the third membrane assembly 103 may have a membrane slightly weaker than the membrane in the membrane assembly 103A to accommodate for loss of pressure in the reactant and sample so that it will break substantially simultaneously. On the other hand, it may be stronger than the membrane 103A so that the pressure builds to a higher level after a period of time in the reactant before breaking through the membrane within the membrane assembly 103.

The membrane assemblies are inserted into the cartridge by unthreading the portions of the cartridge where they are joined at the location for the membrane assembly such as at 210 in FIG. 2 where the bottom tubular wall 205 has an internally threaded upper portion and the bottom of the tubular wall 204 having external threads are threaded together. The joints where they meet are angled and the membrane assembly 103 fits in those joints. Similarly, the membrane assemblies 103 and 103A in FIG. 3 fit within similar combinations of threaded female and male joints threaded together where the walls make an angle to receive the membrane assembly. Any other fastening means may be used but it is desirable for the tubes to be separable at the membrane for easy removal and filling of the chambers and replacement of fractured membranes.

Figure 4:
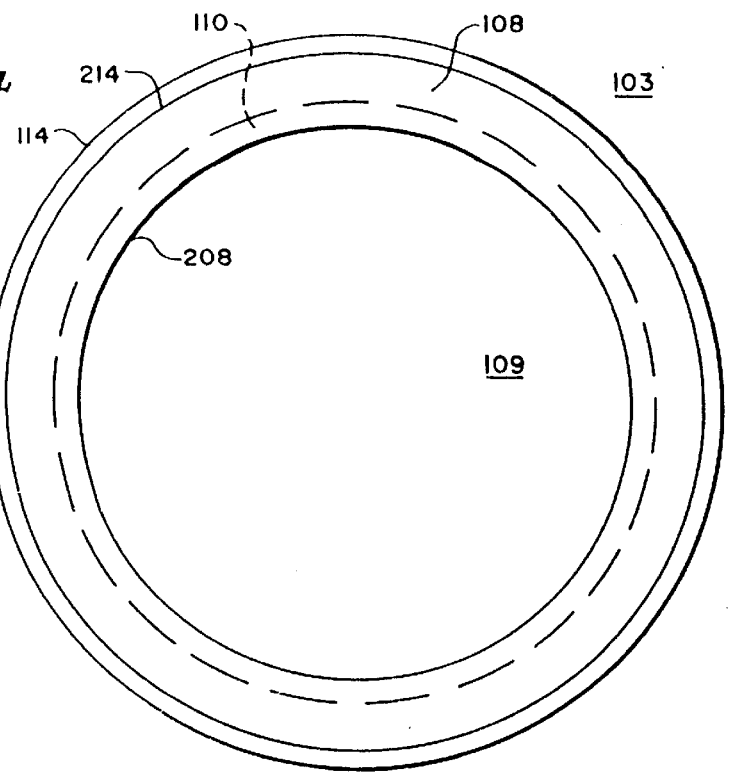
FIG. 4 is a plan view of a membrane assembly used in the embodiment of FIGS. 2 and 3.

In FIG. 4, there is shown a top view of the membrane assembly 103 having a center membrane 109, a top ring 108 and a bottom ring 110. The top ring has an upper surface with its radially outward edge ending at the circular corner 214 and its radially inward circular corner 208. The upper ring slants downwardly to a bottom surface and is radially outward so as to end at the circular lower edge 114 to form the top half of a beveled inwardly beveled outer surface that fits within a v-shaped groove in the tubular walls 204 and 205 where the tubular walls are joined so as to hold the membrane assembly 103 in place. The bottom ring (not shown in FIG. 4) underlies the top ring and is interlocked therewith by an upwardly extending ledge 110 in a manner to be described more fully hereinafter.

The membrane 109 forming the circular center that is clamped between the upper and lower rings 108 and 110 is fluid tight within the ring and has a strength that permits rupture under predetermined pressure but resists rupturing at pressures lower than the predetermined pressure. The predetermined pressure is selected to provide a consistent starting pressure and flow rate for the supercritical fluid flowing through the cartridge before it carries sample downwardly through the cartridge. Sample is positioned above the top membrane in most applications but can be at other locations supported by a membrane or by the bottom surface of the cartridge. Membranes can also hold a reactant or modifier so that when the supercritical fluid fractures the membrane, the reactant or modifier drops down to the level of the sample and the sample is extracted, although this is not the most common mode intended for the cartridge 30 or 30A. Similarly, membranes may be located so that the extracting fluid is altered by a reactant after breaking a seal above the reactant compartment and/or after breaking the supporting reactant.

Figure 5:
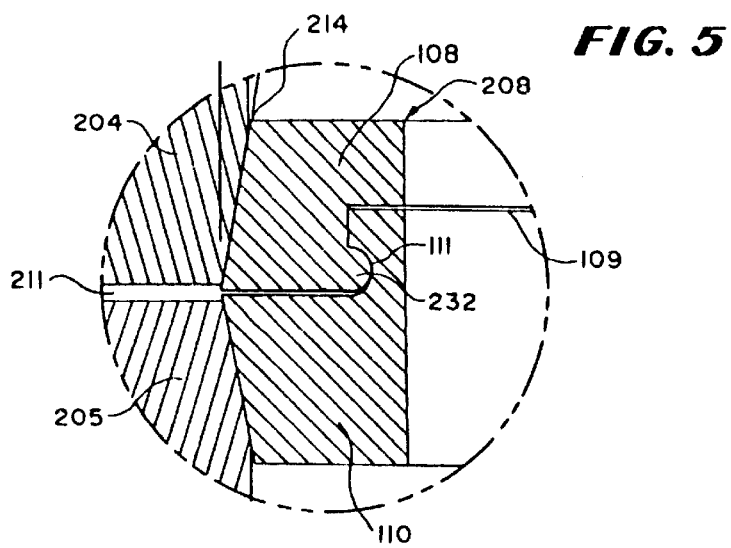
FIG. 5 is a fragmentary sectional view of a portion of the embodiment of FIG. 4.

In FIG. 5 there is shown a fragmentary sectional view of a portion of the upper tubular wall 204, the lower tubular wall 205, the upper ring 108 and the lower ring 110 in place where the tubular wall 205 engages the tubular wall 204 with the internal threads of an outwardly extending portion on the tubular wall 205 (FIG. 2) engaging external threads on the bottom portion of the tubular wall 204 (FIG. 2). At these locations, the inner surfaces of the tubular wall 204 slant downwardly and radially outwardly from the longitudinal axis of the tubular wall at an angle with respect to the vertical and the wall portion 205 has a similar angle with respect to the vertical slanting radially outwardly from the bottom edge of the lower ring 110 up to the center point to form an annular surface circling the cartridge wall in the form of an indentation.

A corresponding slope is found on the upper ring 108 and one on the lower ring 110 to form a radially outwardly extending annular surface that fits within the annular indentation in the inner wall of the cartridge to hold the membrane in place. The two peaks of the inward indentation of the cartridge inner wall and the outward indentation of the upper and lower rings 108 and 110 meet at the horizontal annular ring between the abutting sides of the threaded portion of the upper tube 204 and the lower tube 205 indicated at 211. The membrane 109 extends as a dividing horizontal circular area in the vertical tube through the mating points of the upper and lower rings that hold it in place and stretch it between the chambers 104 and 105.

In the preferred embodiment, the slope of the annular groove in the tube walls and the slope of the outward edge formed by the upper and lower rings 108 and 110 is 10 degrees. However, they can be any suitable number of degrees or any shape, providing they can mount a pressure sensitive fluid seal in place to separate the chambers.

Figure 6:
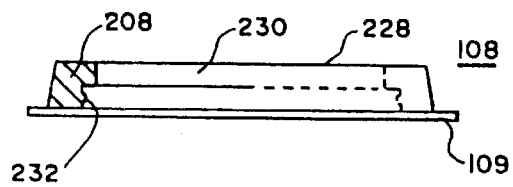
FIG. 6 is a sectional view of a portion of the membrane assembly used in the embodiment of FIG. 2.

In FIG. 6, there is shown a partly elevational, partly sectional view of the upper ring 108 having a portion 208 to the left of its center line that is sectioned and a portion to the right of its center line 228 that is in elevation. As shown in this view, the upper ring has a hollow center portion 230 with downwardly extending end portions each having extending inwardly, an abutement 232 which encircles an inner portion of the ring. This abutement 232 serves as a locking engagement with the lower ring to hold the membrane 109 within the ring.

Figure 7:
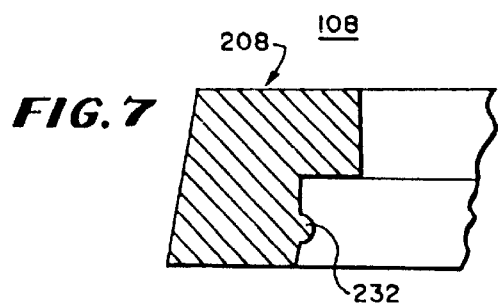
FIG. 7 is a fragmentary sectional view of a portion of the membrane assembly of FIG. 6.

In FIG. 7, there is an enlarged fragmentary view of the sectioned portion 208 of the upper ring 108 showing the locking detent 232. As shown in this view, the detent 232 is circular and extends outwardly from the inner wall of a short cylinder at the bottom of the upper ring to project radially inwardly in a manner that will be described hereinafter that conforms with a radially inwardly annular groove in the lower ring.

Figure 8:
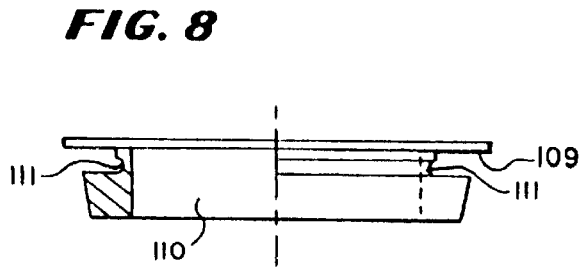
FIG. 8 is an elevational view partly sectioned of a portion of the membrane assembly used in the embodiment of FIG. 1.

In FIG. 8, there is shown a partially elevational and partially sectioned view of the lower ring 110 with an annular upper groove 111 extending inwardly and coforming to the shape of the radially inwnardly extending detent 232 so that the upper and lower section may be locked together with the ring detent 232 fitting within the groove 111 and holding there between the membrane 109.

Figure 9:
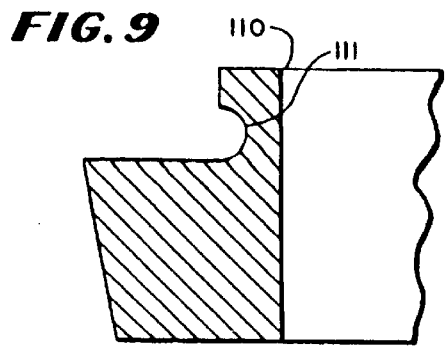
FIG. 9 is a sectional view of a portion of the embodiment of FIG. 8.

In FIG. 9, there is shown a fragmentary view of the sectioned portion of the lower ring 110 showing an enlarged form the annular inwardly extending groove 111. The upper and lower ring members are easily assembled and disassembled to the wall portions 204 and 205 (FIG. 5) because the individual compartments of the cartridges are threaded together and separated from each other by unthreading using a torque of less than 35 inch pounds. The rupture membrane assembly 103 seal is comprised of an upper seal 108, a rupture membrane 109 and a lower seal 110. The upper and lower seals may be snapped together with a snap member 111, or used with another fastener.

In the preferred embodiment of the invention, the seals 108 and 110 are constructed of polyetheretherketone or other suitable material. Both ends of tube 104 and the female end of tube 105 have corresponding 10 degree beveled edges. The membrane 109 is constructed of aluminium or other suitable material. Membrane thickness is from $1/10,000$ inch to $3/1000$ inch with the preferred embodiment of $5/10,000$ inch.

One function of the cartridge is in neutral oil and loss determination employing supercritical fluid extraction. The accuracy and precision of the supercritical fluid extraction neutral oil and loss determination is a function of consistent and reproducible initiation of the determination. Consistent intitation of the method can be achieved by the apparatus described above. Supercritical fluid extraction neutral oil and loss determination can be performed more quickly than by prior art, the supercritical fluid extraction determination method can be automated, consumes little or no organic solvent and is less labor intensive.

In supercritical fluid extraction neutral oil and loss determination, the sample cartridge functions in the following manner. Upper and lower rings 108, 110 and membrane 109 are assembled together to form a rupture seal. The rupture seal is inserted into the beveled annular groove at the end of a tube 104. The tube 105 is threaded and hand tightened into tube 104, securing the rupture seal between tube 104 and 105. The securing of the rupture seal forms a liquid tight closure between the chambers. The sample cartridge is used in a vertical position such that tube 104 is above tube 105. Therefore, tube 104 constitutes the top chamber and tube 105 constitutes the bottom chamber.

Once the sample cartridge is assembled and the rupture membrane or membranes is or are in place, the cartridge is inverted such that tube 105 is upward. The chamber created by assembly 105 is then filled to capacity with activated alumina 113 or other suitable material. Excess alumina is removed from the exterior of the sample cartridge. Tube 105 is closed by positioning frit 106 at the end of assembly 105 and secured by hand tightening the bottom end cap 107. The cartridge is then placed vertically such that tube 104 is upward. The appropriate amount of oilseed oil sample 134 is placed into the chamber assembly 104. The chamber is then closed by positioning frit 102 and hand tightening the top end cap 101. The rupture seal prevents the contact or intermixing of contents in the upper and lower chambers of the sample cartridge. The seal remains intact until the seal is broken by pressurization of the cartridge 30 or 30A.

The sample cartridge must be used in conjunction with a supercritical fluid extractor that utilizes equalized pressure inside and outside of the sample cartridge such as an Isco, Inc., model SFX 2-10, SFX 2-20 or SFX 3560 or other appropriate supercritical fluid extractor. The invention is intended for use with both manual and automated instruments. FIG. 2 illustrates a schematic drawing of an appropriate supercritical fluid extractor similar to U.S. Pat. 5,132, 014.

The sample cartridge containing the alumina and oilseed oil is loaded into the extractor by snapping the nipple of the top end cap 101 (FIG. 1) into the breech plug 32 of the plug assembly 26. The cartridge is then positioned in the pressure vessel 24 and is secured by hand tightening using knob 34. The sample cartridge 30 is now positioned in the supercritical fluid extractor as shown in FIG. 2.

The fluid flow path as shown in FIG. 1 is from pump 12 to the collection vial 98 is as follows. The pump 12 pressurizes the supercritical fluid. The fluid flows through tubing 76, tee 20, tubing 56 to extraction valve 54. When extraction valve 54 is opened, the fluid flows through tubing 58, heat exchanger 40 through tubing 60 and enters the pressure vessel 24. Pressure vessel 24 fills in a manner that simultaneously pressurizes the outside of cartridge 30 from the top, down. Supercritical fluid flows through the cartridge 30 and exits through fitting 46 and tubing 66 into extractant valve 50. When extractant valve 50 is open, fluid is allowed to flow through valve 50 in tubing 68 and eventually through restrictor 128 and into collector 98.

During the period in which the cartridge 30 is being filled, a pressure differential exists between the chamber in upper tube 104, and the chamber in lower tube 105. Due to the pressure differential, rupture membrane 109 is breached eliminating the separation of the two chambers and enables the contents of the chambers to mix. Pressurization of the sample cartridge will consistently and predictably breach the rupture membrane. Therefore contents of the two cartridge chambers can be consistently mixed from experiment to experiment regardless of the amount of time elapsed from the loading of the cartridge.

Figure 10:
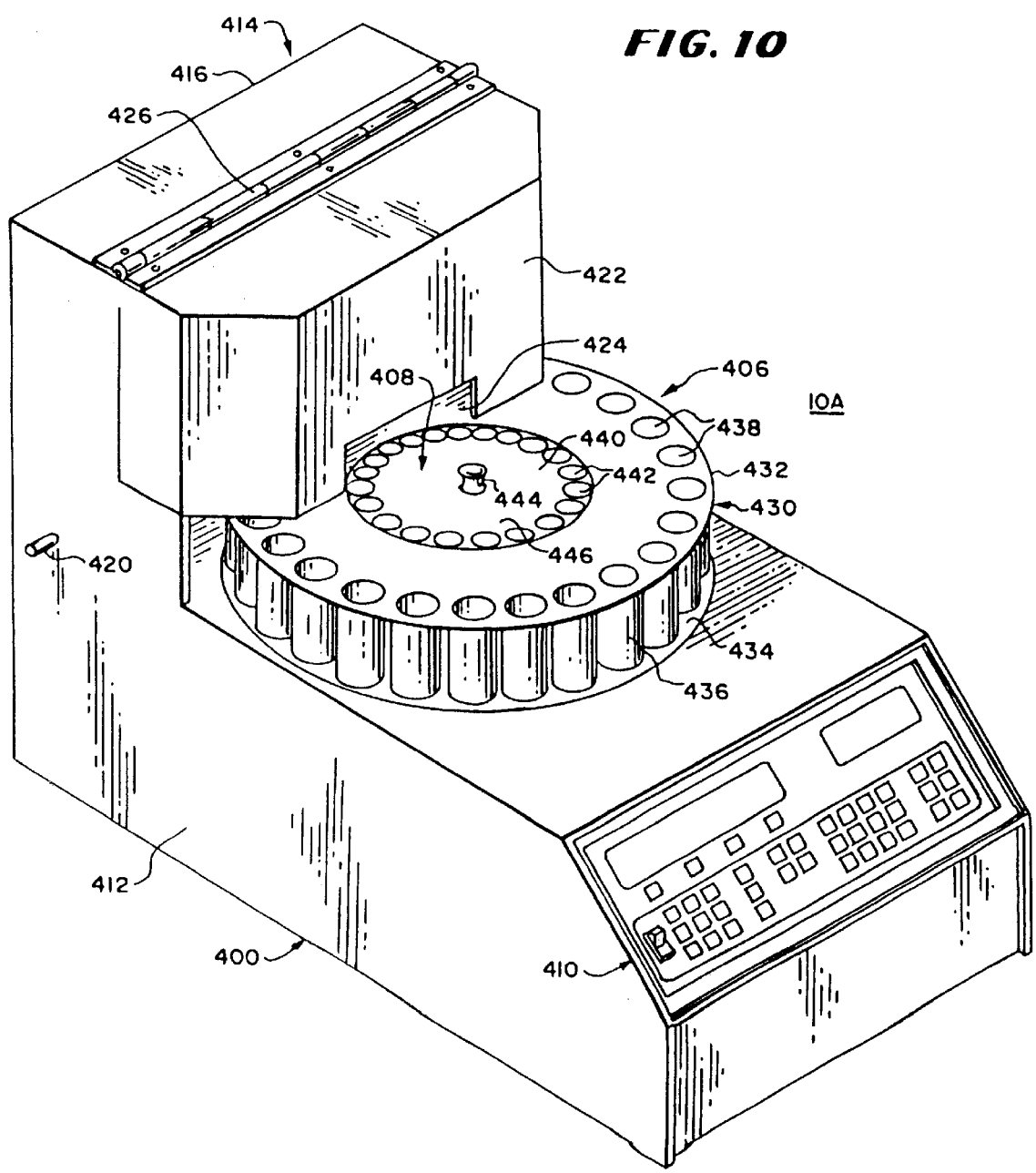
FIG. 10 is a perspective view of an automatic extractor and collector system.

In FIG. 10, there is shown a simplified perspective view of another embodiment 10A of supercritical fluid extraction system having a cabinet 400 containing a drive section in its lower portion (not shown in FIG. 10), an extraction section in the upper portion of the cabinet (not shown in FIG. 10), a sample injection section 406 and a fraction collection section 408. The supercritical liquid extraction system 10A is controlled from a panel 410 on the front of the cabinet 400 and the drive section operates the extraction section, the sample injection section 406, and the fraction collection section 408, which cooperate together to extract a plurality of samples sequentially and collect the extractant from the .pa samples in separate containers with minimum intervention by an operator.

The liquid extraction system in the embodiment 10A operates in a manner similar to that of the embodiment of FIG. 1 but is adapted to cooperate with the novel sample injector and fraction collector. With this arrangement, a series of samples to be extracted are preloaded into a means for holding the samples and the samples are automatically injected one at a time into the extractor. In the extractor, supercritical fluid is supplied to the samples and an extractant is removed from the samples one by one. To aid in correlating the embodiment 10 and the embodiment 10A, similar parts have the same reference numerals but in the embodiment of FIG. 10A, the numerals include the suffix "A".

The extractant is supplied to individual containers or individual compartments of one container in a fraction collector. Thus, a plurality of extractions are performed on a plurality of different preloaded samples without the need for manually loading samples or initiating the flow of the supercritical fluid for each individual sample. The samples are automatically mechanically moved one by one into the extractor for extraction instead of being individually physically injected by an operator.

The cabinet 400 has a lower portion 412 generally shaped as a right regular parallelopiped with an angled control panel 410 and upstanding upper portion 414 which is another right regular parallelopiped extending upwardly to create a profile substantially shaped as an "L" having a common back portion or rear panel 416 which may contain fans and connections for supplementary pumps and the like. A fluid fitting 420 extends from one side to permit near supercritical fluids to be introduced into the cabinet 400. The L-profiled cabinet 400 has an angled front panel 410 for convenient use of controls and a top surface on the foot of the "L" for manipulation of samples to be injected and extractants that are collected.

To permit access to the interior of the cabinet 400, the upper portion 414 includes a hinged front access panel 422 having hinges 426 at its top so that it can be pivoted upwardly. It includes an opening 424 near its bottom to permit the entrance of fraction collector receptacles that are relatively tall. It extends downwardly to a point spaced from the top surface of the lower portion 412 of the cabinet 400 a sufficient distance to permit the entrance of normal receptacles used in the sample injector and the fraction collector.

The sample injection section 406 includes a sample reel 430 which is formed of upper and lower rotatable plates 432 and 434 spaced vertically from each other and containing holes in the upper plate 432 and openings in the lower plate 434 which receive cylindrical tubular sleeves 436 having vertical longitudinal axes and open ends. The upper open end 438 permits samples to be received and to be removed as the sample reel 430 is rotated into the extractor.

With this arrangement, the sample reel 430 may be rotated to move samples one by one into the extractor for processing. The sample reel 430 is horizontal and extends into the upper portion 414 of the cabinet 400 and into the extractor assembly with its vertical center of rotation being outside of the upper portion 414 to permit ready access to a number of the sleeves 436 by users and yet to permit sequential rotation by automatic means into the extractor. In the preferred embodiment, there are 24 sleeves for containing 24 distinctly different samples which can, without human intervention, be moved into the extractor.

To receive extractant, the fraction collection section 408 includes a horizontal fraction collector reel 440 mounted concentrically with the sample reel 430 but having a smaller diameter to be inside the sample reel 430 having a plurality of openings 442 circularly arranged in spaced apart relationship with each other about the periphery of a top plate 446 of the fraction collector reel 440 and having in its center a knob 444 by which the fraction collector reel 440 may be lifted and removed from the cabinet 400. With this arrangement, the fraction collector reel 440 may be lifted and removed or reinserted after the hinged access panel 422 is pivoted upwardly about the hinges 426.

When the fraction collector reel 440 is in place, it is rotated automatically through the opening 424 into a location in which one or more individual containers 442 may receive extractant. The fraction collector reel 440 is moved alternately with the sample reel 430 and independently of it so that, after a sample injection and extraction, one or more of the openings 442 are moved into position .pa to receive the extractant prior to the injection of another sample for extraction.

Because the reels 430 and 440 rotate within the upper portion 414 of the cabinet 400 with a portion of its periphery outside of the cabinet 400, the collected extractant may be removed and new sample added during operation of the equipment. For this purpose, the receptacles for the fractions and the receptacles for the samples have upward open ends and are mounted with their axes vertical.

The invention can also be used for the consistent addition of reactants and/or modifiers during a supercritical fluid extraction or reaction. An example of such a use is the addition of chelating agent during the supercritical fluid extraction of metals from environmental samples. In order for the supercritical fluid extraction of metal to be successful, the metals must be chelated prior to or during extraction. The use of the invention will allow the sample and chelating agent to remain separated until the initiation of the extraction allowing for consistant chelating reaction times, regardless of other variables. In this case, the chelating agent is placed in the top chamber in tube 104 and the metal containing sample is placed in the lower chamber in tube 105. The rupture membrane prevents the initiation of the chelation reaction until extraction cartridge is pressurized.

From the above description, it can understood that the cartridge and supercritical extraction flow system of this invention has several advantages, such as for example: (1) consistent extraction results can be obtained even when being used to assay oilseeds, petroleum or other oil mixtures; (2) stages in the supercritical extraction can be coordinated with pressure through the result of membranes separating stages of the extraction process; and (3) the process is easily subject to automation.

Although a preferred embodiment of the invention has been described with some particularity, many modifications and variations in the invention are possible in the light of the above teachings. Therefore, it is to be understood that, within the scope of the appended claims, the invention may be practiced other than as specifically described.

What is claimed is:

1. A method of supercritical fluid extraction comprising the steps of:
   applying supercritical fluid to a first chamber of a sample cartridge while preventing flow to a second chamber;
   after supercritical fluid has been applied to said first chamber of said cartridge, permitting said supercritical fluid from said first chamber to flow into a second chamber;
   permitting at least a portion of the fluid from said second chamber to be collected.

2. A method in accordance with claim 1 in which the fluid is permitted to flow from said first chamber into said second chamber at a predetermined pressure differential between said first chamber and second chamber.

3. A method in accordance with claim 1 in which the step of applying supercritical fluid to said first chamber includes the step of applying supercritical fluid to a sample in said first chamber.

4. A method in accordance with claim 3 in which the step of permitting fluid to flow from said first chamber into said second chamber includes the step of permitting fluid to flow from said first chamber into said second chamber containing a separating material.

5. A method in accordance with claim 4 in which said fluid is applied to said first chamber at a predetermined pressure less than an operating pressure of said cartridge and released into said second chamber after pressure has equalized between said first chamber and a source of the predetermined pressure whereby the sample may be separated in said second chamber in a sufficiently short period of time to avoid plugging of the separating material in said second chamber.

6. A method in accordance with claim 5 in which said separating material and fluid are used for neutral oil and loss determination.

7. A method according to claim 1 wherein the flow of fluid to the second chamber is blocked by a membrane separating the first and second chambers.

8. A method according to claim 1 in which the flow of fluid to the second chamber is permitted by an increase in pressure in the first chamber beyond a predetermined design pressure.

9. A method according to claim 8 wherein the flow of fluid to the second chamber is blocked by a membrane separating the first and second chambers and the flow of fluid into the second chamber is permitted by causing the membrane to be ruptured by pressure.

10. A method according to claim 1 in wherein the fluid is permitted to flow when a pressure difference between the first and second chambers is at least 20 percent of the operating pressure of the cartridge.

11. A method according to claim 1 wherein extract is assayed after being collected from said second chamber.

12. A method according to claim 11 in which the first chamber includes a sample and the second chamber includes a separating medium.

* * * * *